US00PP21280P3

(12) United States Plant Patent

Nagata et al.

(10) Patent No.: US PP21,280 P3

(45) Date of Patent: Sep. 7, 2010

(54) ST. AUGUSTINE GRASS PLANT NAMED 'NUF-76'

(50) Latin Name: *Stenotaphrum secundatum*
Varietal Denomination: NUF-76

(75) Inventors: Russell T. Nagata, Belle Glade, FL (US); Philip Busey, Davie, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 91 days.

(21) Appl. No.: 11/890,834

(22) Filed: Aug. 8, 2007

(65) Prior Publication Data

US 2008/0184441 P1 Jul. 31, 2008

Related U.S. Application Data

(60) Provisional application No. 60/879,996, filed on Jan. 10, 2007.

(51) Int. Cl.
*A01H 5/00* (2006.01)

(52) U.S. Cl. ..... Plt./392

(58) Field of Classification Search ..... Plt./392
See application file for complete search history.

(56) References Cited

U.S. PATENT DOCUMENTS

| | | | | | |
|---|---|---|---|---|---|
| PP7,699 | P | * | 10/1991 | Busey | Plt./392 |
| PP7,852 | P | * | 4/1992 | Busey | Plt./392 |
| 2009/0199316 | P1 | * | 8/2009 | Philley et al. | Plt./392 |
| 2009/0293164 | P1 | * | 11/2009 | Philley et al. | Plt./392 |

OTHER PUBLICATIONS

Mickie Anderson. UF turfgrass researchers release slow-grow low-mow grass—and it's pretty. University of Florida News Jun. 4, 2007. available at: http://news.ufl.edu/2007/06/04/slow-grass/.*

Rangasamy, M. et al Categories of Resistance in St. Augustinegrass Lines to Southern Chinch Bug (Hemiptera: Blissidate) Plant Resistance J. Econ. Entomol. 99(4): 1446-1451 (2006).*

Cherry et al. Southern Chinch Bug (Hemiptera: Lygaeidae) Survival on St. Augustinegrass Selections. Journal of Entomological Science. vol. 39, No. 4 (Oct. 2004).*

* cited by examiner

*Primary Examiner*—Wendy C. Haas
(74) *Attorney, Agent, or Firm*—Jondle & Associates, P.C.

(57) ABSTRACT

Perennial St. Augustinegrass having plant hopper and southern chinch bug insect resistance, narrow leaf blades and slower leaf extension rates over time when compared with other St. Augustinegrass varieties thus requiring less frequent mowing.

5 Drawing Sheets

Genus and species: *Stenotaphrum secundatum* (Walt.) Kuntze

Variety denomination: NUF-76

BACKGROUND OF THE INVENTION

This invention relates to a new and distinct St. Augustinegrass that is the result of a complex hybridization program to develop a dark green, fine bladed St. Augustinegrass. Parents were selected for darker green foliage color, narrow leaf width, low maintenance and resistance to common insect pests and disease. This genotype was first labeled as FA 1997-108 and evaluated as NUF-76. This selection was propagated vegetatively to provide planting stock for studying performance and distinguishing NUF-76 from other St. Augustinegrass cultivars. The St. Augustinegrass 'NUF-76' has been asexually propagated through vegetative cuttings of stolons in Florida beginning in 2005.

CROSS REFERENCE TO RELATED APPLICATION

This application claims the benefit of U.S. provisional patent, application number 60/879,996 filed Jan. 10, 2007.

SUMMARY OF INVENTION

NUF-76 is a fine bladed, dark green St. Augustinegrass, *Stenotaphrum secundatum* that is resistant to the southern chinch bug, *Blissus insularis* and the plant hopper, *Liburnia pseudoseminigra*. NUF-76 has slow leaf extension growth rates that result in the need for reduced frequency of mowing, there by saving on fuel necessary for lawn maintenance and for wear and tear of the lawn mower.

BRIEF DESCRIPTION OF THE ILLUSTRATIONS

Figure 1:
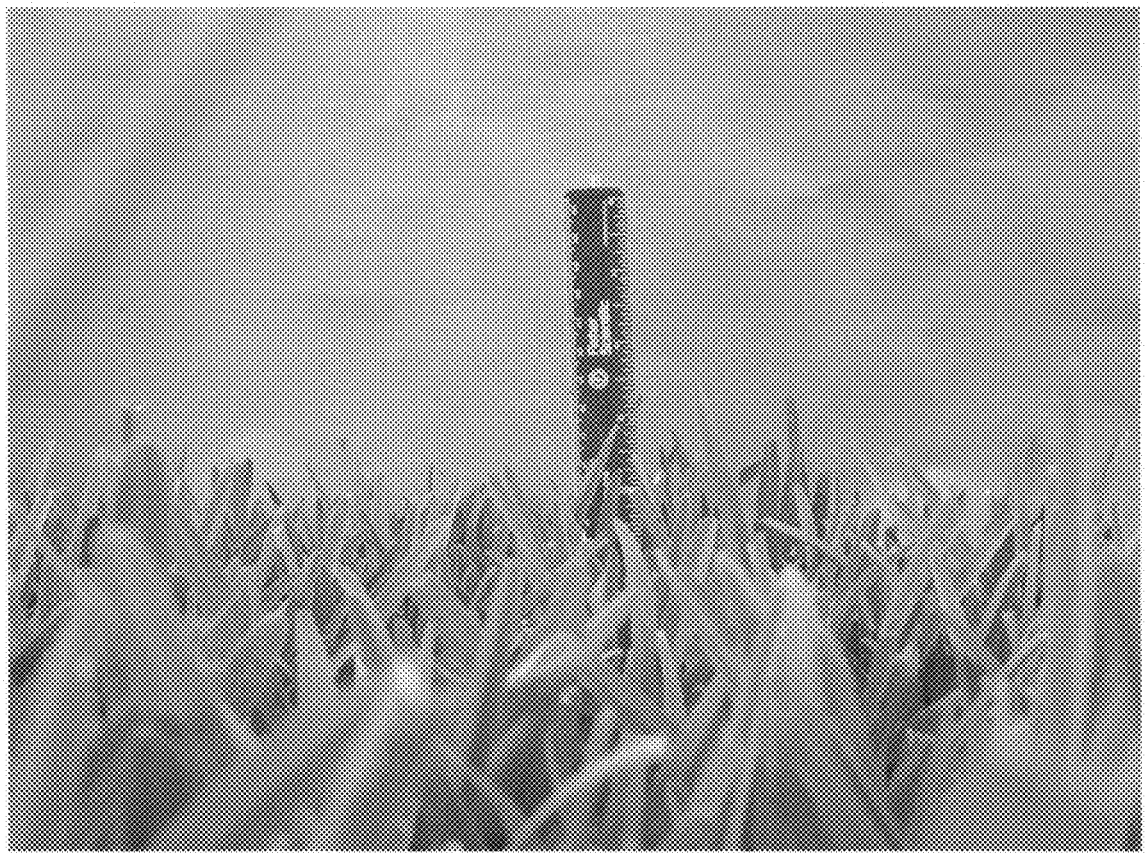

FIG. 1. NUF-76 St. Augustinegrass leaf blade height two weeks since mowing in experiments conducted in the month of July.

Figure 2:
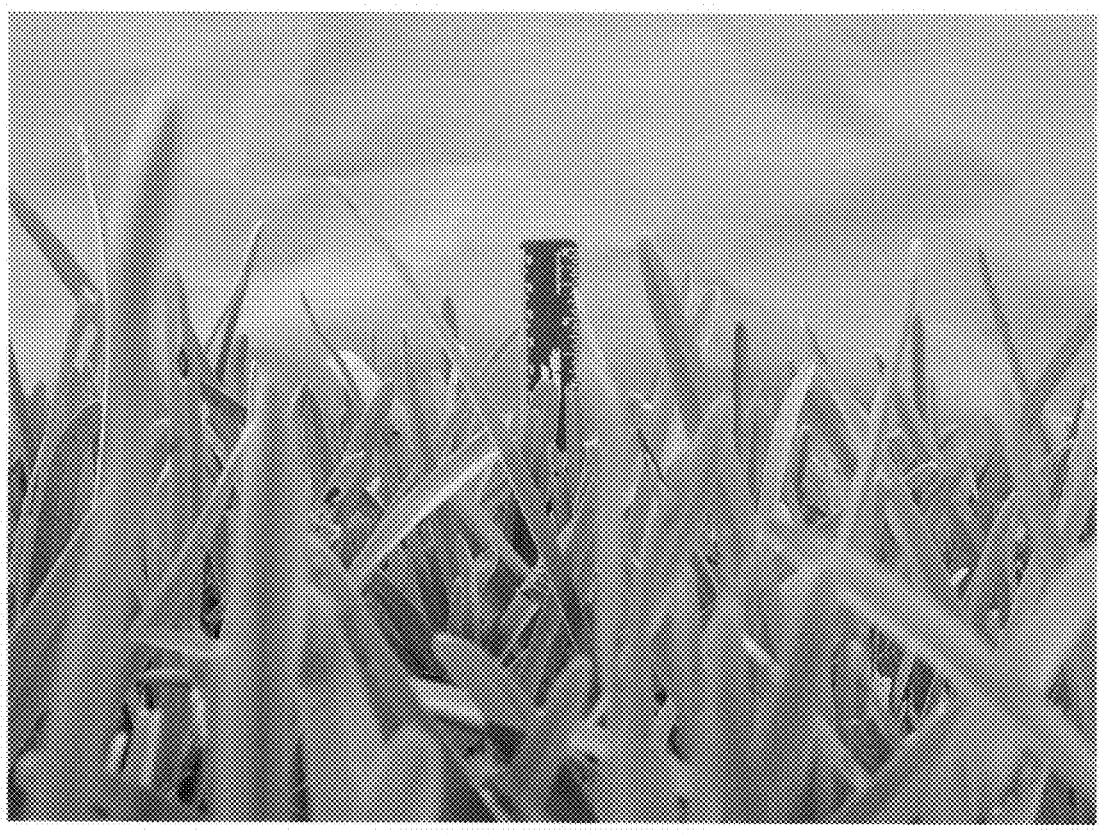

FIG. 2. Floratam St. Augustinegrass leaf blade height two weeks since mowing in experiments conducted in the month of July.

Figure 3:
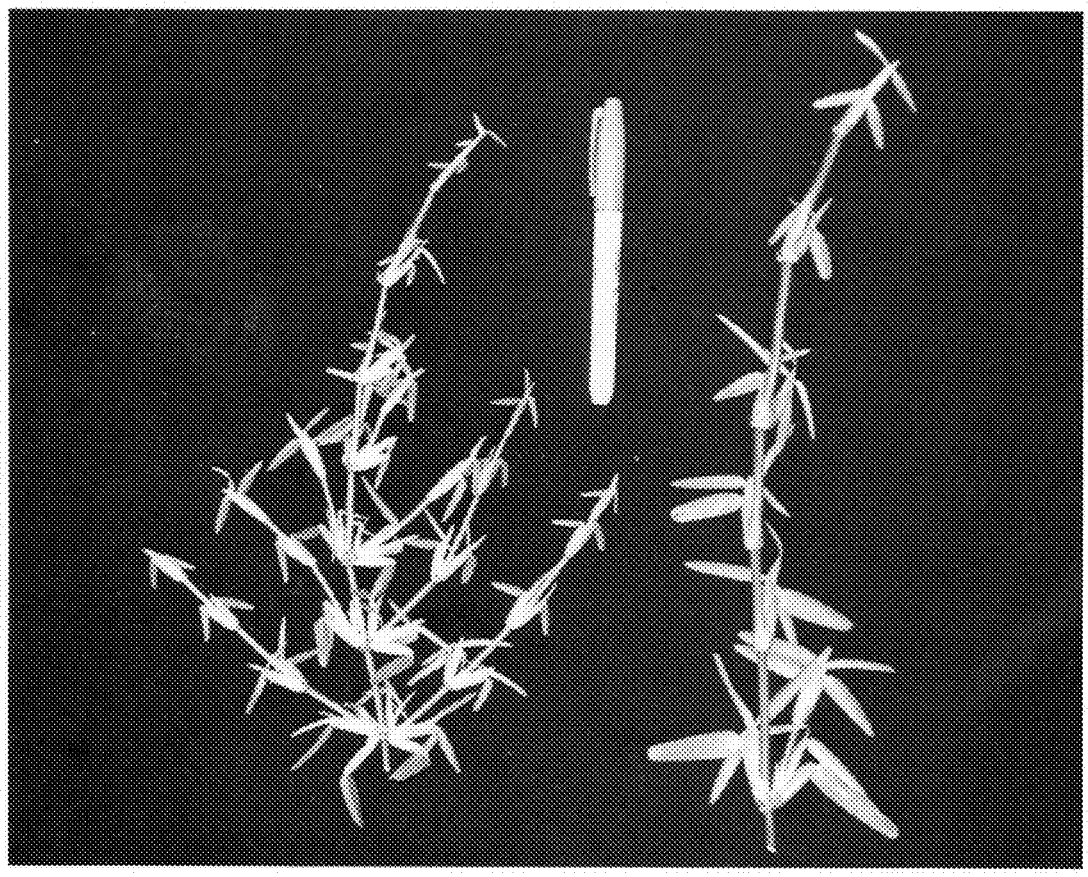

FIG. 3. Comparison of Floratam (left) and NUF-76 (right) runner growth and internode lengths.

Figure 4:
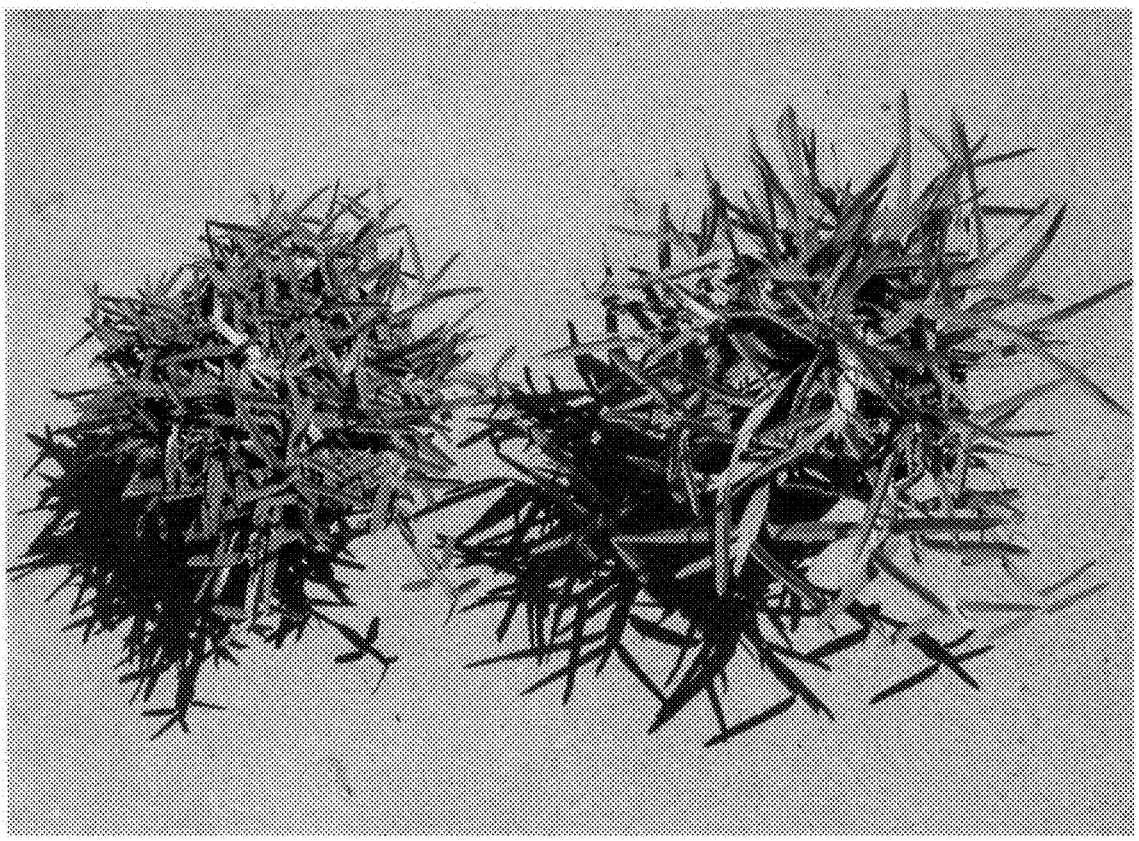

FIG. 4. Comparison of shoot and leaf density of Floratam (right) and NUF-76(left).

Figure 5:
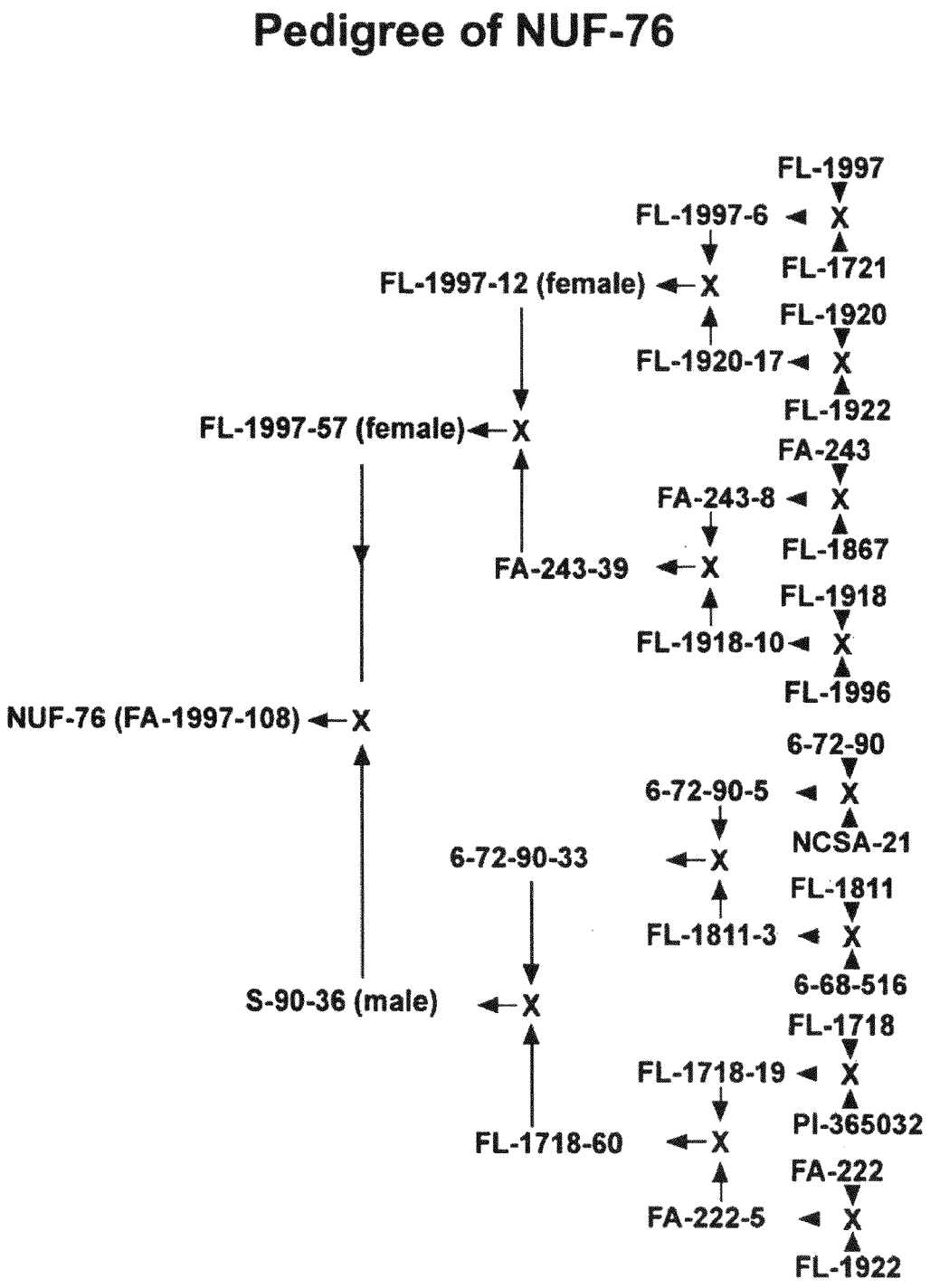

FIG. 5. Pedigree of NUF-76 St. Augustinegrass.

DETAILED DESCRIPTION OF THE VARIETY

Insect and Disease Resistance

NUF-76 is resistant to two common insect pests, the southern chinch bug, *Blissus insularis* and the plant hopper (Tables 1 and 2). NUF 76 is the first St. Augustinegrass known to the inventor reported to have resistance to the plant hopper, *Liburnia pseudoseminigra*. Plant hoppers feeding solely on NUF-76 survive 3.2 days on average compared with susceptible host plants in which they survived 11.2 or more days. Reproduction occurred on the susceptible host Classic and Palmetto, as evident by nymph production.

TABLE 1

Survival *Liburnia pseudoseminigra* plant hopper on NUF-76 and comparison St. Augustinegrasses[2].

| Variety/Selection | Days of Survival |
|---|---|
| Classic[1] (unpatented) | 18.2 a |
| Palmetto[1] (U.S. Plant Pat. No. 9395) | 13.0 ab |
| Bitterblue[1] (unpatented) | 11.2 b |
| Seville[1] (U.S. Plant Pat. No. 4097) | 8.2 be |
| Floratam (unpatented) | 3.4 c |
| FX-10 (U.S. Plant Pat. No. 7852) | 3.4 c |
| NUF-216 (unpatented) | 3.2 c |
| FSHA-115 (unpatented) | 3.2 c |
| NUF-76 | 3.2 c |
| Floralawn (unpatented) | 2.6 c |

[1]Plant hoppers survived past the 20 day duration of this experiment, at which point host plant fitness to support plant hopper survival diminishes.
[2]Means followed by the same letter are not significantly different (alpha = 0.05) using a protected LSD test (SAS 1996)

NUF-76 is resistant to all tested populations of southern chinch bugs from the state of Florida, including those that kill Floratam. For many southern chinch bug populations, mortality on NUF-76 was 100% within the 14 day test period. Chinch bug survival was significantly higher for Floratam and Floratine. Mortality on NUF-76 was similar to FX-10 and NUF-216, both selections having large leaves compared to NUF-76.

TABLE 2

Percent mortality of southern chinch bug, *Blissus insularis* feeding on NUF-76 and comparison St. Augustinegrass held two weeks on each cultivar. Chinch bugs collected from nine cities or their suburbs in geographic regions of Florida[1].

| Variety | Mortality (%) | SD | Range |
|---|---|---|---|
| FX-10 | 94.9 a | 10.3 | 69-100 |
| NUF-216 | 94.6 a | 9.6 | 71-100 |
| NUF-76 | 91.3 a | 12.1 | 63-100 |
| Floratine (unpatented) | 60.6 b | 23.8 | 14-95 |
| Floratam | 47.2 b | 27.9 | 0-71 |

[1]Means followed by the same letter are not significantly different (P = 0.05) using a protected LSD test (SAS 1996).

Leaf Extension Rate

Leaf extension rate of NUF-76 was always shorter than all other St. Augustinegrass varieties known to the inventor, but was always statistically equal to Seville. Leaf extension rate of NUF-76 was equal to Seville and FX-10 and significantly less than NUF-216 and Floratam seven days after mowing. At 14 days after mowing, leaf growth was similar to Seville and FX-10. NUF-76 was half the height of Floratam and 60% the height of NUF-216. Three weeks after mowing, leaf growth of NUF-76 averaged 7.6 cm which was similar to Seville and 2.5 times shorter than Floratam. NUF-76 is shorter after 21 days of growth, than Floratam after 7 days. Using cultivars with slower leaf extension rates such as NUF-76 can reduce the frequency of mowing, thereby reducing the amount of fuel required to maintain a lawn and also reduce wear and tear of the mower. In a state such as Florida where more than 4 million acres of turfgrass is managed, elimination of a single mowing will result in significant fuel savings.

TABLE 3

Leaf blade growth of NUF-76 and comparison St. Augustinegrasses one, two and three weeks after mowing[1].

| | Leaf Growth from Last Mowing (cm) | | |
|---|---|---|---|
| Variety | 7 days | 14 days | 21 days |
| NUF-76 | 3.8 c | 6.0 c | 7.6 d |
| Seville | 5.4 c | 6.3c | 8.4 d |
| FX-10 | 4.6 c | 7.4 c | 10.3 c |
| NUF-216 | 7.2 b | 9.8 b | 13.6 b |
| Floratam | 9.6 a | 13.0 a | 19.0 a |

[1]Means followed by the same letter are not significantly different (P = 0.05) using a protected LSD test (SAS 1996).

Leaf Morphology

Unmowed NUF-76 has significantly shorter, narrowest, and smallest leaf area of comparison St. Augustinegrass cultivars. These reduced leaf characteristics result in NUF-76 appearance to be a fine leaf textured St. Augustinegrass with a dense and compact canopy. NUF-76 average leaf length measured 106.5 mm and a width of 6.7 mm. These measurements resulted in average leaf area of 62.6 square mm, 68% the area of its closest comparison variety.

TABLE 4

Measurements of leaf characteristics of NUF-76 and comparison St. Augustinegrasses[1].

| Variety | Leaf Length (mm) | Leaf Width (mm) | Leaf Area ($mm^2$) |
|---|---|---|---|
| NUF-76 | 106.5 d | 6.7 d | 62.6 d |
| Seville | 130.2 c | 8.0 c | 91.7 c |
| FX-10 | 153.2 b | 9.2 a | 122.3 b |
| NUF-216 | 170.2 b | 8.0 b | 116.7 b |
| Floratam | 204.4 a | 9.0 a | 154.7 a |

[1]Means followed by the same letter are not significantly different (P = 0.05) using a protected LSD test (SAS 1996).

Reproductive Structures

Inflorescences of NUF-76 are terminal and auxiliary, averaging 1.85 panicles per flowering culm. Mean spike length of NUF-76 is 97.75 mm, equal in shortness to 1997-6 and shorter than other cultivars. Floral region measurements averaged 57.35 mm for NUF-76 which was shorter than all cultivars known to the inventor except for FX-10. Spiklet or seed number per inflorescence was 25, equal to Floratam, Seville and Raleigh for the lowest number. Stigmas are white and anther sac color is yellow.

TABLE 5

Inflorescence characteristics NUF-76 and comparison St. Augustinegrass[1].

| Variety | Spike Length (mm) | Floral Region Length (mm) | Number of Spiklets (seeds) | Spike number per shoot |
|---|---|---|---|---|
| FX-10 | 120.8 de | 59.0 d | 39.8 a | 2.3 bcd |
| NUF-216 | 161.8 a | 88.6 b | 36.0 a | 2.8 ab |
| NUF-232 (unpatented) | 132.6 cd | 84.4 b | 30.4 b | 2.7 abc |
| 1997-6 (unpatented) | 107.6 ef | 71.2 c | 29.5 b | 2.8 a |
| Floratam | 153.4 ab | 99.8 a | 28.6 bc | 2.1 d |
| Seville | 121.1 de | 68.6 c | 21.2 d | 2.2 cd |

TABLE 5-continued

Inflorescence characteristics NUF-76 and comparison St. Augustinegrass[1].

| Variety | Spike Length (mm) | Floral Region Length (mm) | Number of Spiklets (seeds) | Spike number per shoot |
|---|---|---|---|---|
| Raleigh (unpatented) | 142.4 bc | 71.3 c | 21.0 d | 2.2 cd |
| NUF-76 | 97.8 f | 57.4 d | 25.0 cd | 1.8 d |

[1]Means followed by the same letter are not significantly different (P = 0.05) using a protected LSD test (SAS 1996).

TABLE 6

Anther and stigma color of NUF-76 and other comparison St. Augustinegrass varieties[1].

| Variety | Anther Color | Stigma Color |
|---|---|---|
| NUF-76 | Yellow | White |
| Seville | Yellow | White hairs/purple shaft |
| Floratam | Orange Yellow | Purple |
| Raleigh | Yellow | White |
| Bitterblue | Orange Yellow | White hairs/purple shaft |
| Palmetto | Orange Yellow | White |

[1]Color as observed at pollen dehiscence.

Growth and Ground Coverage

Growth of NUF-76 lateral shoots was equal to other cultivars at 6 weeks from transplanting rooted cutting into the field. However, at 9 weeks lateral shoot lengths of NUF-76 was the shortest. Internode counts however did not differ among cultivars and reduce lateral length was attributed to shorter internodes. As a result, ground coverage during grow-in after sprigging or plugging a new field by NUF-76 was slowest for all cultivars tested. Starting with 3% coverage by the grass plug, mean coverage by NUF-76 was 27.8% after eight weeks. By 16 weeks of growth, all cultivars had 96% ground coverage or better indicating that coverage by NUF-76 will catch up to the other cultivars and coverage approach 100%.

TABLE 7 shoot length and node count of NUF-76 and comparison St. Augustinegrass[1].

| Variety | Shoot length at 6 weeks (cm) | Number of internodes 6 wks | Shoot length at 9 weeks | Number of internodes 9 weeks |
|---|---|---|---|---|
| NUF-76 | 10.1 a | 4.0 ab | 30.2 c | 8.4 a |
| Seville | 17.0 a | 4.6 a | 49.0 b | 9.5 a |
| FX-l0 | 8.9 a | 2.5 b | 40.5 bc | 7.7 a |
| NUF-216 | 16.7 a | 3.8 ab | 61.2 a | 10.2 a |
| Floratam | 15.9 a | 4.6 a | 60.6 a | 10.2 a |

[1]Means followed by the same letter are not significantly different (P = 0.05) using a protected LSD test (SAS 1996).

TABLE 8

Percentage coverage by NUF-76 and other comparison St. Augustinegrasses. Planted Oct. 14, 2004 on 30 cm spacing[1].

| | Percentage of Ground Cover by Turfgrass | | |
|---|---|---|---|
| Variety | 8 weeks Dec. 13, 2004 | 12 weeks Jan. 19, 2005 | 16 weeks Feb. 22, 2005 |
| NUF-76 | 27.5 c | 56.2 c | 96.0 b |
| Floratam | 38.8 b | 83.8 b | 100.0 ab |
| NUF-216 | 48.8 a | 87.5 b | 98.5 a |
| Seville | 47.5 a | 94.2 a | 99.5 a |

[1]Means followed by the same letter are not significantly different (P = 0.05) using a protected LSD test (SAS 1996).

The invention claim is:

1. A new and distinct variety of grass plant as herein described and illustrated.

* * * * *